United States Patent [19]

Brown et al.

[11] Patent Number: 4,489,074
[45] Date of Patent: Dec. 18, 1984

[54] 1,3,4-THIADIAZIN-2-ONES

[75] Inventors: David Brown, Macclesfield; Rodney B. Hargreaves, Poynton; Bernard J. McLoughlin; Stuart D. Mills, both of Macclesfield, all of England

[73] Assignee: Imperial Chemical Industries, PLC, London, England

[21] Appl. No.: 440,857

[22] Filed: Nov. 12, 1982

[51] Int. Cl.³ .................. C07D 285/16; A61K 31/54
[52] U.S. Cl. ......................................... 424/246; 544/8
[58] Field of Search ............................ 544/8; 424/246

[56] References Cited

PUBLICATIONS

Lempert-Sreter et al., Acta Chemica Scientiarum Hungaricae, Tomus, 94, (4), pp. 391–401, (1977).
J. Heterocyclic Chemistry, 1970, 7, 927–930; 1974, 11, 755–761; 1978, 15, 1271–1276.
Ege et al., Liebig's Annalen Chem., 1977, 791–799.
Van Alphen, Rec. Trav. Chim., 1929, 48, 417–421.
Chemical Abstracts, 1948, 42, 5918–9; 1956, 50, 7816–7; 1970, 73, 35334.
Sicardi et al., Journal of Pharmaceutical Sciences, 1974, 63, 1336–7.
Curran et al., Journal of Medicinal Chemistry, 1974, 17, 273–286.

*Primary Examiner*—John M. Ford
*Attorney, Agent, or Firm*—Cushman, Darby & Cushman

[57] ABSTRACT

Heterocyclic compounds of the formula

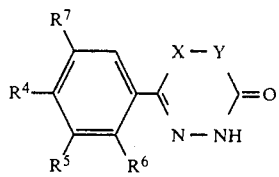

wherein
either X is —CR$^1$R$^2$ and Y is —O—, —S— or —NR$^3$—, wherein R$^1$, R$^2$ and R$^3$, which may be the same or different, each is hydrogen or alkyl of up to 4 carbon atoms;
or X is —O—, —S— or —NH— and Y is —CR$^1$R$^2$— wherein R$^1$ and R$^2$ have the meanings stated above;
wherein either R$^4$ is hydrogen, fluoro or chloro, or alkyl, alkenyl, halogenoalkyl, aminoalkyl, hydroxyalkyl, alkoxyalkyl or alkoxy each of up to 6 carbon atom, and R$^5$, R$^6$ and R$^7$, which may be the same or different, each is hydrogen, fluoro, chloro, bromo or iodo, or alkyl, alkenyl, halogenoalkyl, aminoalkyl, hydroxyalkyl, alkoxyalkyl or alkoxy each of up to 6 carbon atoms, provided that R$^4$, R$^5$, R$^6$ and R$^7$ are not all hydrogen;
or R$^4$ is bromo and R$^5$, R$^6$ and R$^7$ have the meanings stated above, provided that R$^5$, R$^6$ and R$^7$ are not all hydrogen;
or R$^4$ and R$^5$ together, or R$^5$ and R$^6$ together, or R$^4$ and R$^7$ together, form the —CH=CH—CH=CH— group and the other two of R$^4$, R$^5$, R$^6$ and R$^7$ have the meanings stated above; processes for their manufacture and pharmaceutical compositions containing them. The compounds possess cardiotonic and/or antihypertensive activity.

9 Claims, No Drawings

1,3,4-THIADIAZIN-2-ONES

This invention relates to new heterocyclic compounds, some of which possess cardiotonic properties, some of which possess antihypertensive properties and some of which possess both said properties.

Many 6-aryl-dihydropyridazin-3-one derivatives are known which possess pharmaceutical properties affecting the cardiovascular system. These are described for example, in the Journal of Medicinal Chemistry, 1974, 17, 273-286 and in the Journal of Heterocyclic Chemistry, 1974, 11, 755-761, and there is much related patent literature.

When an additional hetero-atom is inserted into the pyridazine nucleus, most of the simple structures have been described in the academic chemical literature. Thus, for example:

2-phenyl-4H,6H-1,3,4-thiadiazin-5-one and its 6-methyl analogue are known from Chemical Abstracts, 1948, 42, 5919 and 1956, 50, 7817;

5-phenyl-3H,6H-1,3,4-thiadiazin-2-one and its 6-methyl analogue are known from Leibig's Annalen der Chemie, 1977, 791 and from this article are also known the corresponding p-bromophenyl and 4-biphenylyl analogues;

2-phenyl-4H,6H-1,3,4-oxadiazin-5-one is known from Receuil des Travaux chimiques des Pays Bas, 1929, 48, 417 and o-hydroxyphenyl analogues thereof are known from J. Heterocyclic Chemistry, 1970, 7; 927;

3-phenyl-4,5-dihydro-5-methyl-1H-1,2,4-triazin-6-one is known from J.Heterocyclic Chemistry, 1978, 15, 1271;

6-phenyl-4,5-dihydro-2H-1,2,4-triazin-3-one and its 4-methyl analogue are known from Chemical Abstracts, 1970, 73, 35334.

From the patent literature 5-phenyl-3H,6H-1,3,4-oxadiazin-2-one and the corresponding 4-bromophenyl and 2-naphthyl analogues are known as blowing agents in the plastics industry, from U.S. Pat. Nos. 4,097,425, 4,105,848 and 4,158,094.

None of the abovementioned references discloses any pharmacological utility for any of the compounds described. The only references to pharmacological activity in this kind of compound of which applicants are aware appear in U.S. Pat. No. 3,514,455, which describes various 4,6-disubstituted-2-phenyl-4H,6H-1,3,4-thiadiazin-5-one derivatives which are claimed to possess antipyretic, analgesic, anti-inflammatory and antiedema activities, and in U.S. Pat. No. 3,946,010, which describes various 3-o-aminophenyl-4,5-dihydro-1H-1,2,4-triazine-6-one derivatives which are claimed to possess anti-inflammatory activity.

A compound of considerable interest at present as a cardiotonic agent is a pyridone derivative known by the name AMRINONE, which has the structure:

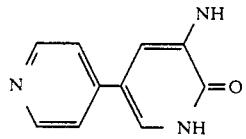

We have now found that various phenylthiadiazinone, oxadiazinone or triazinone derivatives which bear a substituent in one or more of the 2-, 3-, 4- and 5-positions of the phenyl nucleus possess valuable cardiotonic and/or antihypertensive properties.

According to the invention there is provided a heterocyclic compound of the formula:

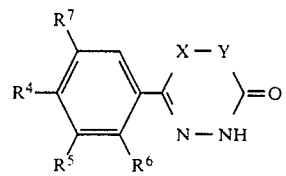

wherein
either X is —CR¹R²— and Y is —O—, —S— or —NR³—, wherein R¹, R² and R³, which may be the same or different, each is hydrogen or alkyl of up to 4 carbon atom;

or X is —O—, —S— or —NH— and Y is —CR¹R²— wherein R¹ and R² have the meanings stated above;

wherein either R⁴ is hydrogen, fluoro or chloro, or alkyl, alkenyl, halogenoalkyl, aminoalkyl, hydroxyalkyl, alkoxyalkyl or alkoxy each of up to 6 carbon atoms, and R⁵, R⁶ and R⁷, which may be the same or different, each is hydrogen, fluoro, chloro, bromo or iodo, or alkyl, alkenyl, halogenoalkyl, aminoalkyl, acylaminoalkyl, hydroxyalkyl, alkoxyalkyl or alkoxy each of up to 6 carbon atoms, provided that R⁴, R⁵, R⁶ and R⁷ are not all hydrogen;

or R⁴ is bromo and R⁵, R⁶ and R⁷ have the meanings stated above, provided that R⁵, R⁶ and R⁷ are not all hydrogen;

or R⁴ and R⁵ together, or R⁵ and R⁶ together, or R⁴ and R⁷ together, form the —CH=CH—CH=CH— group (such that together with the benzene ring they form a naphthalene ring), and the other two of R⁴, R⁵, R⁶ and R⁷ have the meanings stated above.

A suitable value for R¹, R² or R³ when it is alkyl is, for example, methyl or ethyl.

A suitable value for R⁴, R⁵, R⁶ or R⁷ when it is alkyl, alkenyl, halogenoalkyl, aminoalkyl, hydroxyalkyl, alkoxyalkyl or alkoxy is, for example, methyl, ethyl, allyl, chloromethyl, trifluoromethyl, aminomethyl, hydroxymethyl, 2-hydroxyethyl, methoxymethyl, methoxy or ethoxy.

A preferred heterocyclic compound of the invention has the formula stated above wherein either:
X is —CH₂— and Y is —O—, —S—, —NH— or —N(CH₃)—;
or X is —CH(CH₃)— and Y is —S—;
or X is —O—, —S— or —NH— and Y is —CH₂—;
wherein either R⁴ is hydrogen, fluoro, chloro or trifluoromethyl, or alkyl or alkoxy each of up to 4 carbon atoms, and R⁵, R⁶ and R⁷, which may be the same or different, each is hydrogen, fluoro, chloro, bromo, iodo or trifluoromethyl, or alkyl or alkoxy each of up to 4 carbon atoms, provided that R⁴, R⁵, R⁶ and R⁷ are not all hydrogen;
or R⁴ is bromo and R⁵, R⁶ and R⁷ have the last mentioned meanings stated above, provided R⁵, R⁶ and R⁷ are not all hydrogen;
or R⁴ and R⁵ together, or R⁵ and R⁶ together, form —CH=CH—CH=CH— and the other two of R⁴, R⁵, R⁶ and R⁷ are hydrogen.

A particularly preferred heterocyclic compound of the invention has the formula stated above wherein either:

X is —CH₂— and Y is —O—, —S— or —NH—;
or X is —C(CH₃)— and Y is —S—;
or X is —O—, —S— or —NH— and Y is —CH₂—;
wherein R⁴ is hydrogen, fluoro, chloro or trifluoromethyl, or alkyl or alkoxy each of up to 4 carbon atoms, R⁷ is hydrogen and R⁵ and R⁶, which may be the same or different, each is hydrogen, fluoro, chloro, bromo or trifluoromethyl, or alkyl or alkoxy each of up to 4 carbon atoms, provided that R⁴, R⁵ and R⁶ are not all hydrogen.

Specific heterocyclic compounds of the invention are hereinafter described in the Examples. Of these, a preferred compound which possesses cardiotonic activity is 6-(m-chlorophenyl-, m-bromophenyl- or m-trifluoromethylphenyl)-4,5-dihydro-1,2,4-triazin-3(2H)-one, or, especially, 5,6-dihydro-2-(2,4,5-trimethoxyphenyl)-4H-1,3,4-thiadiazin-5-one.

A preferred compound which possesses antihypertensive activity is 5,6-dihydro-2-(m-methoxyphenyl or p-chlorophenyl)-4H-1,3,4-thiadiazin-5-one; or 5-(m-chlorophenyl-, 3,4-dichlorophenyl-, 3,5-dichlorophenyl- or 2-naphthyl-)-3H,6H-1,3,4-thiadiazin-2-one, and of these an especially preferred compound is 5-(3,4-dichlorophenyl)-3H,6H-1,3,4-thiadiazin-2-one.

A preferred process for the manufacture of a compound of the invention wherein X is oxygen or sulphur and Y is —CR¹R²— comprises the reaction of a hydrazide or thiohydrazide of the formula:

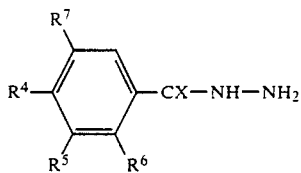

wherein R⁴, R⁵, R⁶ and R⁷ have the meanings stated above and X is sulphur or oxygen, with an acid of the formula:

wherein R¹ and R² have the meanings stated above and wherein hal is a halogen atom, for example the chlorine or bromine atom, or with a reactive derivative thereof.

When X is sulphur the acid is preferably used as a reactive derivative thereof, for example a methyl or ethyl ester, and the reaction may be carried out in aqueous solution, in the presence of a base, for example, sodium hydroxide, at laboratory temperature.

When X is oxygen the acid is preferably used as a reactive derivative thereof, for example the acyl halide, and the reaction carried out in two stages. The benzoylhydrazine may be reacted with the acyl halide in an inert solvent, for example toluene, in the presence of a base, for example potassium carbonate. The diacyl hydrazine thus obtained may then be reacted with a base, for example sodium hydride, in a dipolar aprotic solvent, for example dimethylformamide, or with an alkali metal carbonate in acetone, and the reaction may be carried out at an elevated temperature, for example at about 100° C.

A preferred process for the manufacture of a compound of the invention wherein X is —CR¹R²— and Y is sulphur comprises the reaction of a phenacyl halide of the formula:

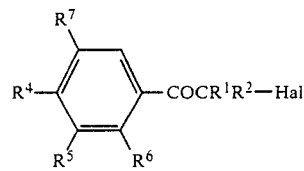

wherein R¹, R², R⁴, R⁵, R⁶, R⁷ and Hal have the meanings stated above, with a thiocarbazate of the formula:

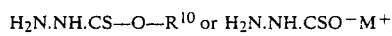

wherein R¹⁰ is alkyl of up to 4 carbon atoms, for example methyl or ethyl, and wherein M⁺ is an alkali metal or ammonium ion.

The reaction may be carried out in an organic diluent or solvent, for example acetonitrile or ethanol, at an elevated temperature, for example at the boiling point of the diluent or solvent.

A preferred process for the manufacture of a compound of the invention wherein X is —CR¹R²— and Y is oxygen comprises the cyclisation of a compound of the formula:

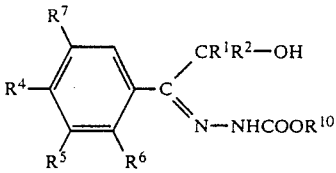

wherein R¹, R², R⁴, R⁵, R⁶, R⁷ and R¹⁰ have the meanings stated above. The cyclisation may be carried out in the presence of a base, for example sodium ethoxide, in a diluent or solvent, for example ethanol, at laboratory temperature.

The starting material for the last-mentioned reaction may be obtained by the reaction of a compound of the formula:

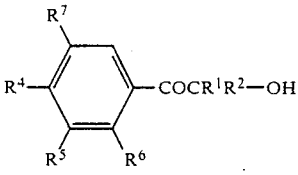

wherein R¹, R², R⁴, R⁵, R⁶ and R⁷ have the meanings stated above, with an alkyl carbazate of the formula:

wherein R¹⁰ has the meaning stated above.

A preferred process for the manufacture of a compound of the invention wherein X is —NH— and Y is —CR¹R²— comprises the reaction of a compound of the formula:

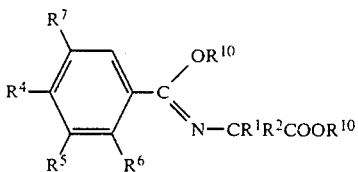

wherein $R^1$, $R^2$, $R^4$, $R^5$, $R^6$, $R^7$ and $R^{10}$ have the meanings stated above (the two $R^{10}$ substituents being the same or different alkyl radicals of up to 4 carbon atoms), with hydrazine.

The reaction may be carried out in a diluent or solvent, for example ethanol, at a temperature up to the boiling point of the diluent or solvent.

The starting material for the last-mentioned reaction may be obtained either by the reaction of a compound of the formula:

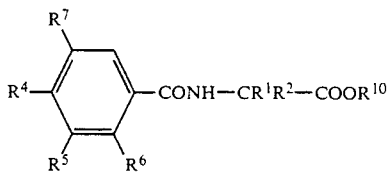

wherein $R^1$, $R^2$, $R^4$, $R^5$, $R^6$, $R^7$ and $R^{10}$ have the meanings stated above, with an oxonium trifluoroborate of the formula $(R^{10})_3OBF_4$, wherein $R^{10}$ has the meaning stated above, or by the reaction of a compound of the formula:

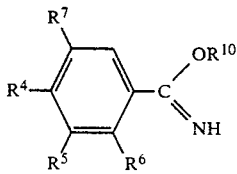

wherein $R^4$, $R^5$, $R^6$, $R^7$ and $R^{10}$ have the meanings stated above, with a glycine ester of the formula $H_2NR^1R^2COOR^{10}$, wherein $R^1$, $R^2$ and $R^{10}$ have the meanings stated above.

A preferred process for the manufacture of a compound of the invention wherein X is $-CR^1R^2-$ and Y is $-NR^3-$ comprises the reaction of a compound of the formula:

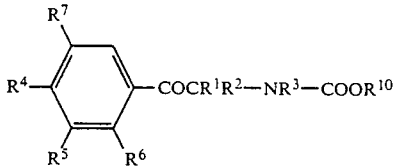

wherein $R^1$, $R^2$, $R^3$, $R^4$, $R^5$, $R^6$, $R^7$ and $R^{10}$ have the meanings stated above, with hydrazine.

The reaction may be carried out in a diluent or solvent, for example ethanol or isopropanol, at a temperature up to the boiling point of the diluent or solvent.

The starting material for the last-mentioned process may be obtained by the reaction of a compound of the formula:

![structure](R4-phenyl-COCR1R2NHR3 with R5, R6, R7)

wherein $R^1$, $R^2$, $R^3$, $R^4$, $R^5$, $R^6$ and $R^7$ have the meanings stated above, with a chloroformate of the formula $R^{10}OCOCl$, wherein $R^{10}$ has the meaning stated above.

A compound of the invention wherein $R^3$ is alkyl may be obtained by the alkylation of the corresponding compound wherein $R^3$ is hydrogen.

As stated above, some of the heterocyclic compounds of the invention possess cardiotonic activity. This may be demonstrated by their ability to increase the rate of change of aortic blood pressure in the anaesthetised cat. At a dose of the compound which produces an effective increase in said rate of change, that is, greater than a 25% increase, no symptom of toxicity is apparent.

As stated above, some of the heterocyclic compounds of the invention possess antihypertensive activity, as demonstrated by their ability to decrease the blood pressure of a normotensive cat or of a spontaneously hypertensive rat. The antihypertensive activity may also be demonstrated by the vasodilation effect produced by the heterocyclic compounds of the invention as shown by their ability to reduce spontaneous contraction in a rat portal vein preparation.

The heterocyclic compound of the invention may be administered to warm-blooded animals, including man, in the form of a pharmaceutical composition comprising as active ingredient at least one heterocyclic compound of the invention in association with a pharmaceutically-acceptable diluent or carrier therefor.

A suitable composition is, for example, a tablet, capsule, aqueous or oily solution or suspension, emulsion, injectable aqueous or oily solution or suspension, dispersible powder, spray or aerosol formulation.

The pharmaceutical composition may contain, in addition to the heterocyclic compound of the invention, one or more drugs selected from sedatives, for example phenobarbitone, meprobamate, chlorpromazine and benzodiazepine sedative drugs, for example chlordiazepoxide and diazepam; vasodilators, for example hydralazine, glyceryl trinitrate, pentaerythritol tetranitrate and isosorbide dinitrate; diuretics, for example chlorothiazide, hydrochlorothiazide, amiloride, bendrofluazide or chlorthalidone; β-adrenergic blocking agents, for example propranolol or atenolol; cardiac membrane stabilising agents, for example quinidine; agents used in the treatment of Parkinson's disease and other tremors, for example benzhexol; and cardiotonic agents, for example digitalis preparations.

When used for the treatment of acute or chronic heart failure or of hypertension in man, it is expected that the heterocyclic compound would be given to man at a total oral dose of between 100 mg. and 2000 mg. daily, at doses spaced at 6–8 hourly intervals, or at an intravenous dose of between 5 mg. and 100 mg.

Preferred oral dosage forms are tablets or capsules containing between 50 and 500 mg., and preferably 100 mg. or 500 mg., of active ingredient. Preferably intravenous dosage forms are sterile aqueous solutions of the heterocyclic compound containing between 0.05% and 1% of active ingredient, and more particularly containing 0.1% w/v of active ingredient.

The invention is illustrated but not limited by the following Examples:

Example 1

A mixture of 2-bromo-p-methoxyacetophenone (4.58 g.), methoxythiocarbonylhydrazine (3.07 g.) and acetonitrile (12.5 ml.) was heated under reflux for 5 hours and then cooled and filtered. The filtrate was evaporated to dryness under reduced pressure and the residue was crystallised from ethanol. There was thus obtained 5-p-methoxyphenyl-3H,6H-1,3,4-thiadiazin-2-one, m.p. 126°–128°.

The process described above was repeated using the appropriate 2-bromo-alkanophenone as starting material (most of these are known compounds, any novel one being prepared by conventional means). There were thus obtained the compounds described in the following table:

extracted three times with ethyl acetate (80 ml. each time) and the extract was washed five times with water (50 ml. each time), dried and evaporated to dryness. The residue was crystallised from ethanol and there was thus obtained 2-m-chlorophenyl-4H,6H-1,3,4-oxadiazin-5-one, m.p. 173°–175° C.

The diacylhydrazine used as starting material was obtained as follows:

Triethylamine (2.8 ml.) was added to a stirred suspension of m-chlorobenzohydrazide (3.4 g.) in dioxan (100 ml.), followed by chloroacetyl chloride (1.5 ml.) added dropwise, and the mixture was stirred for 24 hours and then evaporated to dryness under reduced pressure.

There was thus obtained as residue N-m-chlorobenzoyl-$N^1$-chloroacetylhydrazine, which was used without further purification.

The process described above was repeated except that the appropriate benzohydrazide was used as initial starting material in place of m-chlorobenzohydrazide. There were thus obtained the compounds described in the following table:

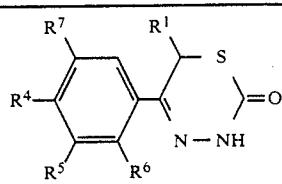

| $R^1$ | $R^7$ | $R^4$ | $R^5$ | $R^6$ | m.p. (°C.) | Crystallisation Solvent |
|---|---|---|---|---|---|---|
| H | H | H | F | H | 144–146 | ethanol |
| H | H | F | H | H | 189–191 | methanol |
| H | H | H | H | Cl | 169–172 | ethyl acetate/petroleum ether (b.p. 40–60° C.) |
| H | H | H | Cl | H | 142–144 | toluene |
| H | H | Cl | H | H | 185–187 | ethanol |
| H | H | F | Cl | H | 176–178 | methanol |
| H | H | Cl | Cl | H | 184–187 | methanol |
| H | Cl | H | Cl | H | 164–165 | isopropanol |
| H | H | Br | Cl | H | 189–191 | isopropanol |
| H | H | Cl | Br | H | 182–185 | methanol |
| H | H | CH$_3$O | Cl | H | 160–161 | isopropanol |
| H | H | CH$_3$ | Cl | H | 150–152 | cyclohexane/ethyl acetate |
| H | Cl | Br | Cl | H | 178–179 | cyclohexane |
| H | H | H | Br | H | 136–137 | methanol |
| H | H | H | J | H | 151–153 | ethyl acetate/petroleum ether (b.p. 40–60° C.) |
| H | H | H | CF$_3$ | H | 154–157 | toluene |
| H | H | H | CH$_3$O | H | 161–162 | ethanol |
| H | H | CH$_3$O | CH$_3$O | H | 157–159 | methanol |
| H | CH$_3$O | CH$_3$O | H | CH$_3$O | 116–121 | aqueous methanol |
| H | CH$_3$O | CH$_3$O | CH$_3$O | H | 189–191 | acetonitrile |
| H | H | iso-C$_4$H$_9$ | H | H | 134–135 | cyclohexane |
| H | H | CH$_3$ | CH$_3$ | H | 133–135 | ethanol |
| CH$_3$ | H | H | Cl | H | 138–139 | ethyl acetate/petroleum ether (b.p. 40–60° C.) |
| CH$_3$ | H | Cl | Cl | H | 168–170 | methanol |
| H | H | H | —CH=CH—CH=CH— | H | 198–199 | methanol |
| H | H | —CH=CH—CH=CH— | H | H | 175–177 | acetone |
| CH$_3$ | H | —CH=CH—CH=CH— | H | H | 183–185 | methanol |

Example 2

Sodium hydride (1.0 g. of a 50% suspension in mineral oil) was added to a solution of N-m-chlorobenzoyl-$N^1$-chloroacetylhydrazine (4.69 g.) in dimethylformamide (100 ml.) and the mixture was heated at 120°–130° C. for 2 hours, cooled, diluted with saturated aqueous sodium chloride solution (200 ml.) and acidified to pH 6 with aqueous 2N-hydrochloric acid. The mixture was

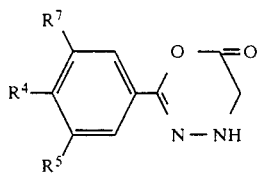

| $R^7$ | $R^4$ | $R^5$ | m.p. (°C.) | Crystallisation Solvent |
|---|---|---|---|---|
| H | methoxy | H | 161–163 | methanol* |
| H | fluoro | H | 190–192 | methanol |
| chloro | H | chloro | 178–180 | isopropanol+ |

*The intermediate N—p-methoxybenzoyl-N—$^1$-chloroacetylhydrazine had m.p. 185–188° C. after crystallisation from ethyl acetate.
+ The intermediate N—(3,5-dichlorobenzoyl)-N$^1$chloroacetylhydrazine had m.p. 222–223° C.

Example 3

A mixture of ethyl p-trifluoromethylhippurate [13.0 g; m.p. 140°–142° C.; prepared from p-trifluoromethylbenzoic acid (12.8 g.), thionyl chloride (75 ml.) and ethyl glycinate hydrochloride (16.35 g.)], triethyloxonium fluoroborate (11.2 g.) and methylene chloride (75 ml.) was stirred at laboratory temperature for 6 days. A solution of potassium carbonate (13.8 g.) in water (20 ml.) was added, the mixture was shaken, and the organic phase was separated, dried and evaporated to dryness. The residue was stirred with petroleum ether and the mixture was filtered. The filtrate was evaporated to dryness and the residual ethyl N-(ethoxycarbonylmethyl)-p-trifluoromethylbenzimidate (12.0 g.) was dissolved in ethanol (50 ml.). Hydrazine hydrate (2 ml.) was added and the mixture was heated under reflux for 2 hours, cooled and filtered. The solid product was crystallised from methanol and there was thus obtained 3-p-trifluoromethylphenyl-4,5-dihydro-1,2,4-triazin-6(1H)-one, m.p. 225°–226° C.

The process described above was repeated except that the appropriate ethyl hippurate was used as starting material in place of ethyl p-trifluoromethyl hippurate. There were thus obtained the compounds described in the following table:

| $R^7$ | $R^4$ | $R^5$ | $R^6$ | m.p. (°C.) | crystallisation solvent |
|---|---|---|---|---|---|
| H | Cl | H | H | 274–277 | methanol |
| H | CH$_3$ | H | H | 259–266 | methanol |
| H | CH$_3$O | H | H | 181–185 | methanol |
| H | C$_2$H$_5$O | H | H | 204–205 | methanol |
| H | (CH$_3$)$_2$CHO | H | H | 216 | ethyl acetate/methanol |
| H | CH$_3$CH$_2$CH$_2$O | H | H | 203–205 | methanol |
| H | H | Cl | H | 218–221 | methanol |
| H | H | Br | H | 234–237 | ethanol |
| H | H | CF$_3$ | H | 196–199 | methanol |
| H | H | CH$_3$O | H | 179–181 | ethyl acetate/methanol |
| H | H | CH$_3$ | H | 197–201 | methanol |

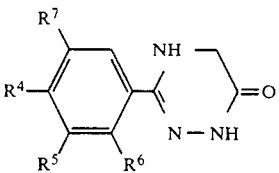

| $R^7$ | $R^4$ | $R^5$ | $R^6$ | m.p. (°C.) | crystallisation solvent |
|---|---|---|---|---|---|
| CH$_3$O | CH$_3$O | H | CH$_3$O | 167–169 | acetonitrile |
| CH$_3$O | CH$_3$O | CH$_3$O | H | 199–202 | acetonitrile |

Example 4

A stirred mixture of methyl N-(2-m-bromophenyl-2-oxoethyl)carbamate (9.67 g.), hydrazine hydrate (3.6 ml.), water (100 ml.) and isopropanol (50 ml.) was heated at 90°–100° C. for 3 days, cooled and filtered. The product was crystallised from methanol and there was thus obtained 6-m-bromophenyl-4,5-dihydro-1,2,4-triazin-3(2H)-one, m.p. 223°–225° C.

The methyl carbamate used as starting material was obtained as follows:

A solution of bromine (7.18 ml.) in methylene chloride (20 ml.) was added to a stirred solution of m-bromoacetophenone (25.6 g.) in methylene chloride (80 ml.) and the mixture was stirred for 30 minutes and then evaporated to dryness under reduced pressure. The residue was crystallised from methanol and there was thus obtained m-bromophenacyl bromide.

A solution of m-bromophenacyl bromide (38.9 g.) in methylene chloride (50 ml.) was added to a stirred solution of hexamethylenetetramine (20.1 g.) in methylene chloride (230 ml.) and the mixture was stirred at laboratory temperature for 2 hours and then filtered. The solid residue (after washing with methylene chloride and drying) was added to a stirred mixture of ethanol (100 ml.) and concentrated aqueous hydrochloric acid (45 ml.) and the mixture was stirred at laboratory temperature for 17 hours and filtered. The solid product was washed with ethanol, and there was thus obtained 2-m-bromophenyl-2-oxoethylamine hydrochloride.

A solution of methyl chloroformate (33.5 ml.) in ethyl acetate (20 ml.) was added to a stirred mixture of the above hydrochloride (42.75 g.) water (370 ml.), benzyltriethylammonium chloride (0.2 g.) and ethyl acetate (350 ml.), and the mixture was stirred at 5° C. Sodium bicarbonate (74 g.) was added portionwise and the mixture was stirred at laboratory temperature for 15 hours. Ethyl acetate (200 ml.) was added and the organic layer was separated. The aqueous layer was extracted twice with ethyl acetate (75 ml. each time) and the combined organic solutions were washed with water (50 ml.) and saturated aqueous sodium chloride solution (50 ml.), dried over magnesium sulphate and evaporated to dryness under reduced pressure. The residue was crystallised for ethyl acetate and there was thus obtained methyl N-(2-m-bromophenyl-2-oxoethyl)carbamate, m.p. 101°–103° C.

The process described above was repeated using the appropriate methyl or ethyl* N-(2-phenyl-2-oxoethyl)carbamate as starting material, and there were thus obtained the compounds described in the following tables:

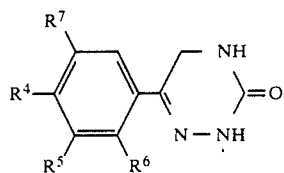

| R⁷ | R⁴ | R⁵ | R⁶ | m.p. (°C.) | Crystallisation Solvent |
|---|---|---|---|---|---|
| H | H | chloro | H | 229–230 | methanol[1] |
| H | H | methoxy | H | 207–209 | methanol* |
| H | H | trifluoro-methyl | H | 196–197 | toluene*[2] |
| H | H | H | methoxy | 198–200 | methanol* |
| H | methoxy | H | H | 220–231 | ethanol |
| H | methyl | methyl | H | 261–263(d) | ethanol |
| H | chloro | chloro | H | 248–251 | ethyl acetate*[3] |
| methoxy | methoxy | methoxy | H | 195–196 | aqueous methanol* |
| H | —CH=CH—CH=CH— | | H | 283–286 | methanol/*ethyl acetate |

[1] The intermediate methyl N—(2-m-chlorophenyl-2-oxoethyl)carbamate has m.p. 93–95° C.

[2] The intermediate 2-m-trifluoromethylphenyl-2-oxoethylamine hydrochloride has m.p. 237–239° C., and the intermediate ethyl N—(2-m-trifluorophenyl-2-oxoethyl)carbamate has m.p. 64–66° C.

[3] The intermediate ethyl N—[2-(3,4-dichlorophenyl)-2-oxoethyl]carbamate has m.p. 96–100° C.

Example 5

Ethyl bromoacetate (5.0 g.) was added to a stirred suspension of 2,4-dimethoxythiobenzohydrazide (6.5 g.) in aqueous 3N-sodium hydroxide solution (25 ml.) and the mixture was stirred at 25° C. for 18 hours and then filtered. The solid product was purified by flash chromatography on a silica gel column (Merck 9385) using a 30:1 v/v mixture of chloroform and methanol as eluant. The aqueous filtrate was acidified with aqueous 2N hydrochloric acid and the mixture was filtered. The solid products, both from the chromatographic purification and from the acidification, were combined and crystallised from aqueous methanol. There was thus obtained 2-(2,4-dimethoxyphenyl)-4H,6H-1,3,4-thiadiazin-5-one, m.p. 162°–164° C.

The 2,4-dimethoxythiobenzohydrazide used as starting material was obtained as follows:

A stirred mixture of 2,4-dimethoxybenzaldehyde (16.6 g.), morpholine (40 g.) and sulphur (4.0 g.) was heated under reflux for 45 minutes and then poured into water (500 ml.). The oil which formed was separated and stirred with water, and the mixture was filtered. There was thus obtained as solid product 2,4-dimethoxythiobenzoylmorpholine, m.p. 103°–105° C.

A mixture of the above compound (20 g.) and hydrazine hydrate (50 ml.) was stirred at 25° C. for 9 days, then at 65° C. for 24 hours and finally at 25° C. for 3 days, filtered and the filtrate was evaporated to dryness under reduced pressure. There was thus obtained as residue 2,4-dimethoxythiobenzohydrazide which was used without further purification.

The process described in the first paragraph above was repeated using the appropriate thiobenzohydrazide as starting material and there were thus obtained the compounds described in the following table:

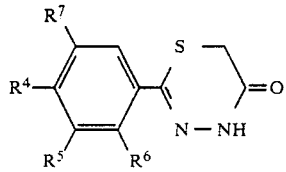

| R⁷ | R⁴ | R⁵ | R⁶ | m.p. (°C.) | Crystallisation Solvent |
|---|---|---|---|---|---|
| H | H | H | methoxy | 140–142 | methanol |
| H | H | methoxy | H | 128–129 | aqueous ethanol |
| H | methoxy | H | H | 162–165 | aqueous ethanol |
| methoxy | H | H | methoxy | 174 | methanol |
| H | H | methoxy | methoxy | 169–170 | methanol |
| H | methoxy | methoxy | H | 197–198 | methanol/methylene chloride |
| methoxy | H | methoxy | H | 149–152 | aqueous methanol |
| methoxy | methoxy | H | methoxy | 125–126 | acetonitrile |
| methoxy | methoxy | methoxy | H | 136–137 | aqueous methanol |
| H | H | chloro | H | 161–162 | ethyl acetate |
| H | chloro | H | H | 182–183 | ethyl acetate |
| H | chloro | chloro | H | 177–180 | methanol |

The thio-benzohydrazides used as starting materials were prepared by a similar process to that described in the second and third paragraphs above, except that in two instances piperidine was used in place of morpholine. For those compounds wherein R⁶ is hydrogen, the lengthy (13 day) process described in the third paragraph above was completed in 24 hours. The intermediate thiobenzoylmorpholines and thiobenzoylpiperidines have the melting points shown in the following tables:

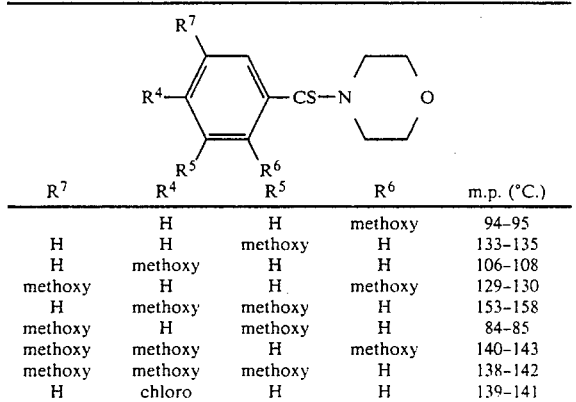

| $R^7$ | $R^4$ | $R^5$ | $R^6$ | m.p. (°C.) |
|---|---|---|---|---|
| H | H | H | methoxy | 94–95 |
| H | H | methoxy | H | 133–135 |
| H | methoxy | H | H | 106–108 |
| methoxy | H | H | methoxy | 129–130 |
| H | methoxy | methoxy | H | 153–158 |
| methoxy | H | methoxy | H | 84–85 |
| methoxy | methoxy | H | methoxy | 140–143 |
| methoxy | methoxy | methoxy | H | 138–142 |
| H | chloro | H | H | 139–141 |

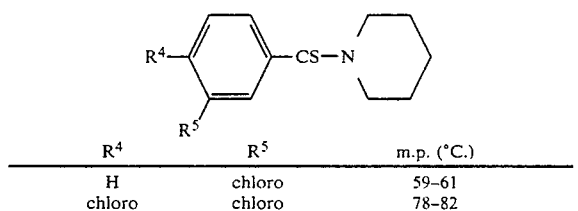

| $R^4$ | $R^5$ | m.p. (°C.) |
|---|---|---|
| H | chloro | 59–61 |
| chloro | chloro | 78–82 |

Example 6

Sodium hydride (0.1 g. of a 50% dispersion in mineral oil) was added to a stirred solution of 2-hydroxy-m-chloroacetophenone ethoxycarbonylhydrazone (3.6 g.) in ethanol (175 ml.) and the mixture was stirred at 25° for 18 hours and then filtered. The solid product was crystallised from ethyl acetate and there was thus obtained 5-(m-chlorophenyl)-3H,6H-1,3,4-oxadiazin-2-one, m.p. 168°–170° C.

The 2-hydroxy-m-chloroacetophenone ethoxycarbonylhydrazone used as starting material was obtained as follows:

Iodobenzene diacetate (32.2 g.) was added during 15 minutes to a stirred solution of m-chloroacetophenone (15.4 g.) and potassium hydroxide (28.0 g.) in methanol (300 ml.) which was kept at 0° C., and the mixture was allowed to warm up to laboratory temperature, stirred at that temperature for 2 hours and then evaporated to dryness under reduced pressure. The residue was shaken with water (200 ml.) and diethyl ether (200 ml.) and the ethereal solution was separated, dried over magnesium sulphate and evaporated to dryness. A mixture of the residue, ethanol (35 ml.) and aqueous 2N-hydrochloric acid (35 ml.) was stirred at 25° C. for 20 hours and then filtered, and the solid product was crystallised from methanol. There was thus obtained 2-hydroxy-m-chloroacetophenone, m.p. 103°–105° C.

A mixture of the above compound (5.5 g.), ethyl carbazate (3.3 g.) and ethanol (150 ml.) was stirred at 25° C. for 60 hours and then concentrated to small volume by evaporation. The residue was heated until a clear solution was obtained, and was then cooled and filtered. There was thus obtained as solid residue 2-hydroxy-m-chloroacetophenone ethoxycarbonylhydrazone, m.p. 109°–110° C.

The process described above was repeated except that the appropriate acetophenone was used as initial starting material. There were thus obtained the compounds described in the following table:

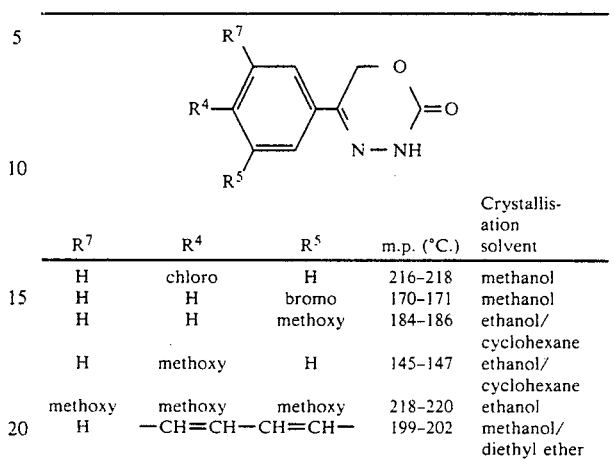

| $R^7$ | $R^4$ | $R^5$ | m.p. (°C.) | Crystallisation solvent |
|---|---|---|---|---|
| H | chloro | H | 216–218 | methanol |
| H | H | bromo | 170–171 | methanol |
| H | H | methoxy | 184–186 | ethanol/cyclohexane |
| H | methoxy | H | 145–147 | ethanol/cyclohexane |
| methoxy | methoxy | methoxy | 218–220 | ethanol |
| H | —CH=CH—CH=CH— | | 199–202 | methanol/diethyl ether |

The intermediates which were characterised have the melting points shown in the following tables:

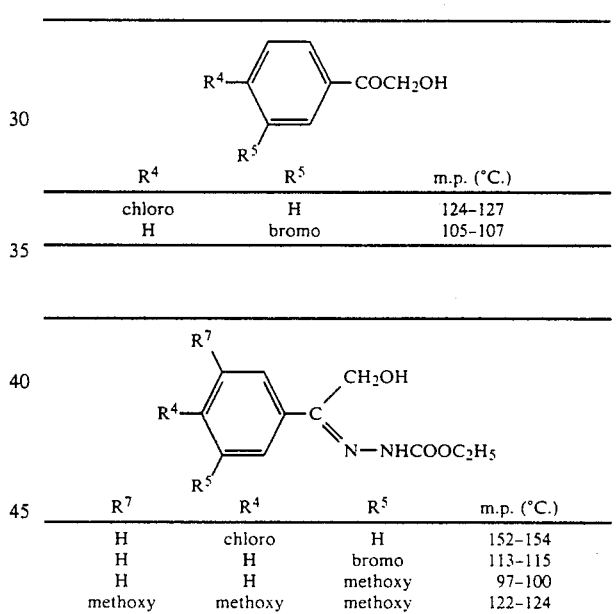

| $R^4$ | $R^5$ | m.p. (°C.) |
|---|---|---|
| chloro | H | 124–127 |
| H | bromo | 105–107 |

| $R^7$ | $R^4$ | $R^5$ | m.p. (°C.) |
|---|---|---|---|
| H | chloro | H | 152–154 |
| H | H | bromo | 113–115 |
| H | H | methoxy | 97–100 |
| methoxy | methoxy | methoxy | 122–124 |

Example 7

Sodium hydride (0.41 g. of a 50% dispersion in mineral oil) was added to a stirred solution of 6-m-chlorophenyl-4,5-dihydro-1,2,4-triazin-3(2H)-one (Example 4; 21.1 g.) in dimethylformamide (50 ml.) and after effervescence had ceased methyl iodide (0.59 ml.) was added. The mixture was stirred at 25° C. for 3 hours, allowed to stand for 20 hours and then evaporated to dryness under reduced pressure. Tetrachloroethylene was added and removed by evaporation three times, and the residue was purified by chromatography on a silica gel column using a 50:1 v/v mixture of chloroform and methanol as eluant. The solid product was washed with diethyl ether and there was thus obtained 6-m-chlorophenyl-4,5-dihydro-4-methyl-1,2,4-triazin-3(2H)-one, m.p. 116°–117° C.

What we claim is:

1. A heterocyclic compound of the formula

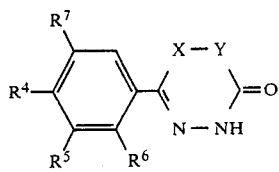

wherein X is $-CR^1R^2$ and Y is $-S-$ wherein $R^1$ and $R^2$ which may be the same or different, each is hydrogen or alkyl of up to 4 carbon atoms;

wherein either $R^4$ is hydrogen, fluoro or chloro, or alkyl, alkenyl, halogenoalkyl, aminoalkyl, hydroxyalkyl, alkoxyalkyl or alkoxy each of up to 6 carbon atom, and $R^5$, $R^6$ and $R^7$, which may be the same or different, each is hydrogen, fluoro, chloro, bromo or iodo, or alkyl, alkenyl, halogenoalkyl, aminoalkyl, hydroxyalkyl, alkoxyalkyl or alkoxy each of up to 6 carbon atoms, provided that $R^4$, $R^5$, $R^6$ and $R^7$ are not all hydrogen;

or $R^4$ is bromo and $R^5$, $R^6$ and $R^7$ have the meanings stated above, provided that $R^5$, $R^6$ and $R^7$ are not all hydrogen;

or $R^4$ and $R^5$ together, or $R^5$ and $R^6$ together, or $R^4$ and $R^7$ together, form the $-CH=CH-CH=CH-$ group and the other two of $R^4$, $R^5$, $R^6$ and $R^7$ have the meanings stated above.

2. A heterocyclic compound as claimed in claim 1 wherein

X is $-CH_2-$
or $-CH(CH_3)-$ and Y is $-S-$;

wherein either $R^4$ is hydrogen, fluoro, chloro or trifluoromethyl, or alkyl or alkoxy each of up to 4 carbon atoms and $R^5$, $R^6$ and $R^7$, which may be the same or different, each is hydrogen, fluoro, chloro, bromo, iodo or trifluoromethyl, or alkyl or alkoxy each of up to 4 carbon atoms, provided that $R^4$, $R^5$, $R^6$ and $R^7$ are not all hydrogen;

or $R^4$ is bromo and $R^5$, $R^6$ and $R^7$ have the meanings stated above, provided that $R^5$, $R^6$ and $R^7$ are not all hydrogen;

or $R^4$ and $R^5$ together, or $R^5$ and $R^6$ together, form $-CH=CH-CH=CH-$ and the other two of $R^4$, $R^5$, $R^6$ and $R^7$ are hydrogen.

3. A heterocylic compound as claimed in claim 1 wherein

X is $-CH_2-$ $-C(CH_3)-$ and Y is $-S-$;

wherein $R^4$ is hydrogen, fluoro, chloro or trifluoromethyl, or alkyl or alkoxy each of up to 4 carbon atoms, $R^7$ is hydrogen and $R^5$ and $R^6$, which may be the same or different, each is hydrogen, fluoro, chloro, bromo or trifluoromethyl, or alkyl or alkoxy each of up to 4 carbon atoms, provided that $R^4$, $R^5$ and $R^6$ are not all hydrogen.

4. The compound 5-(m-chlorophenyl)-3H,6H-1,3,4-thiadiazin-2-one.

5. The compound 5-(3,5-dichlorophenyl)-3H,6H-1,3,4-thiadiazin-2-one.

6. The compound 5-(2-naphthyl)-3H,6H-1,3,4-thiadiazin-2-one.

7. The compound 5-(3,4-dichlorophenyl)-3H,6H-1,3,4-thiadiazin-2-one.

8. A pharmaceutical composition possessing cardiotonic properties or antihypertensive properties or the combination thereof, said composition comprising as active ingredient at least one heterocyclic compound, claimed in claim 1, in association with a pharmaceutically-acceptable diluent or carrier therefor.

9. A method for the treatment of acute or chronic heart failure in a warm-blooded animal in need of such treatment, which comprises administering to said animal an effective amount of a heterocyclic compound claimed in claim 1.

* * * * *